US009624237B2

(12) United States Patent
Pi et al.

(10) Patent No.: US 9,624,237 B2
(45) Date of Patent: Apr. 18, 2017

(54) ORIDONIN FUNCTIONALIZED SELENIUM NANOPARTICLES AND METHOD OF PREPARATION THEREOF

(71) Applicant: Macau University of Science and Technology, Macau (MO)

(72) Inventors: Jiang Pi, Taipa (MO); Jiye Cai, Taipa (MO); Hua Jin, Taipa (MO)

(73) Assignee: Macau University of Science and Technology, Macau (MO)

( * ) Notice: Subject to any disclaimer, the term of this patent is extended or adjusted under 35 U.S.C. 154(b) by 154 days.

(21) Appl. No.: 14/744,040

(22) Filed: Jun. 19, 2015

(65) Prior Publication Data

US 2016/0257694 A1 Sep. 8, 2016

(30) Foreign Application Priority Data

Mar. 5, 2015 (CN) .......................... 2015 1 0101642

(51) Int. Cl.
*C07D 493/08* (2006.01)
(52) U.S. Cl.
CPC .................. *C07D 493/08* (2013.01)
(58) Field of Classification Search
CPC .................................................. C07D 493/08
USPC .................................................. 428/402, 403
See application file for complete search history.

(56) References Cited

U.S. PATENT DOCUMENTS

2012/0028916 A1* 2/2012 Fournial ................ A61K 8/347
514/33

OTHER PUBLICATIONS

Bo Yu et al., "Positive Surface Charge . . . of Selenium Nanoparticles" ACS Aug. 9, 2012, 51, 8956-8963.*
Wen Liu et al., "Selenium Nanoparticles as a Carrier . . . " ACS NANO, 2012, vol. 6, No. 8, 6578-6591.*
Dongdong Sun et al., "The effects of luminescent . . . " Biomaterials 34 (2013) 171-180.*
T. Ikezoe, S.S. Chen, X.J. Tong, D. Heber, H. Taguchi, H.P. Koeffler, Oridonin induces growth inhibition and apoptosis of a variety of human cancer cells, Int J Oncol, 23 (2003) 1187-1193.
C.Y. Li, E.Q. Wang, Y. Cheng, J.K. Bao, Oridonin: An active diterpenoid targeting cell cycle arrest, apoptotic and autophagic pathways for cancer therapeutics, Int J Biochem Cell Biol, 43 (2011) 701-704.
R. Zeng, Y. Chen, S. Zhao, G.H. Cui, Autophagy counteracts apoptosis in human multiple myeloma cells exposed to oridonin in vitro via regulating intracellular ROS and SIRT1, Acta Pharmacol Sin, 33 (2012) 91-100.
F.H. Gao, F. Liu, W. Wei, L.B. Liu, M.H. Xu, Z.Y. Guo, W. Li, B. Jiang, Y.L. Wu, Oridonin induces apoptosis and senescence by increasing hydrogen peroxide and glutathione depletion in colorectal cancer cells, Int J Mol Med, 29 (2012) 649-655.
J. Huang, L.J. Wu, S. Tashiro, S. Onodera, T. Ikejima, Reactive oxygen species mediate oridonin-induced HepG2 apoptosis through p53, MAPK, and mitochondrial signaling pathways, J Pharmacol Sci, 107 (2008) 370-379.
L.H. Ye, W.J. Li, X.Q. Jiang, Y.L. Chen, S.X. Tao, W.L. Qian, J.S. He, Study on the autophagy of prostate cancer PC-3 cells induced by oridonin, Anat Rec (Hoboken), 295 (2012) 417-422.
Y.H. Zhang, Y.L. Wu, S. Tashiro, S. Onodera, T. Ikejima, Reactive oxygen species contribute to oridonin-induced apoptosis and autophagy in human cervical carcinoma HeLa cells, Acta Pharmacol Sin, 32 (2011) 1266-1275.
J.B. Liu, J.Y. Yue, Preliminary study on the mechanism of oridonin-induced apoptosis in human squamous cell oesophageal carcinoma cell line EC9706, J Int Med Res, 42 (2014) 984-992.
M.P. Rayman, The importance of selenium to human health, Lancet, 356 (2000) 233-241.
C. Rock, P.J. Moos, Selenoprotein P regulation by the glucocorticoid receptor, Biometals, 22 (2009) 995-1009.
W.F. Fang, A.J. Han, X.L. Bi, B. Xiong, W.C. Yang, Tumor inhibition by sodium selenite is associated with activation of c-Jun NH2-terminal kinase 1 and suppression of beta-catenin signaling, International Journal of Cancer, 127 (2010) 32-42.
A. Tabassum, R.G. Bristow, V. Venkateswaran, Ingestion of selenium and other antioxidants during prostate cancer radiotherapy: a good thing?, Cancer Treat Rev, 36 (2010) 230-234.
H.L. Wang, J.S. Zhang, H.Q. Yu, Elemental selenium at nano size possesses lower toxicity without compromising the fundamental effect on selenoenzymes: Comparison with selenomethionine in mice, Free Radical Biology and Medicine, 42 (2007) 1524-1533.
L. Kong, Q. Yuan, H. Zhu, Y. Li, Q. Guo, Q. Wang, X. Bi, X. Gao, The suppression of prostate LNCaP cancer cells growth by Selenium nanoparticles through Akt/Mdm2/AR controlled apoptosis, Biomaterials, 32 (2011) 6515-6522.
Y. Li, X. Li, Y.S. Wong, T. Chen, H. Zhang, C. Liu, W. Zheng, The reversal of cisplatin-induced nephrotoxicity by selenium nanoparticles functionalized with 11-mercapto-1-undecanol by inhibition of ROS-mediated apoptosis, Biomaterials, 32 (2011) 9068-9076.
Y. Huang, L. He, W. Liu, C. Fan, W. Zheng, Y.S. Wong, T. Chen, Selective cellular uptake and induction of apoptosis of cancer-targeted selenium nanoparticles, Biomaterials, 34 (2013) 7106-7116.
D. Sun, Y. Liu, Q. Yu, Y. Zhou, R. Zhang, X. Chen, A. Hong, J. Liu, The effects of luminescent ruthenium(II) polypyridyl functionalized selenium nanoparticles on bFGF-induced angiogenesis and AKT/ERK signaling, Biomaterials, 34 (2013) 171-180.
W. Liu, X.L. Li, Y.S. Wong, W.J. Zheng, Y.B. Zhang, W.Q. Cao, T.F. Chen, Selenium Nanoparticles as a Carrier of 5-Fluorouracil to Achieve Anticancer Synergism, ACS Nano, 6 (2012) 6578-6591.
Y. Xiao, Z.T. Lin, Y. Chen, H. Wang, Y.L. Deng, D.E. Le, J. Bin, M. Li, Y. Liao, Y. Liu, G. Jiang, High molecular weight chitosan derivative polymeric micelles encapsulating superparamagnetic iron oxide for tumor-targeted magnetic resonance imaging, Int J Nanomedicine, 10 (2015) 1155-1172.
K. Zhao, Y. Zhang, X.Y. Zhang, C. Shi, X. Wang, X.H. Wang, Z. Jin, S.J. Cui, Chitosan-coated poly(lactic-co-glycolic) acid nanoparticles as an efficient delivery system for Newcastle disease virus DNA vaccine, Int J Nanomed, 9 (2014) 4609-4619.
B. Yu, Y. Zhang, W. Zheng, C. Fan, T. Chen, Positive surface charge enhances selective cellular uptake and anticancer efficacy of selenium nanoparticles, Inorg Chem, 51 (2012) 8956-8963.

* cited by examiner

*Primary Examiner* — Leszek Kiliman
(74) *Attorney, Agent, or Firm* — Spruson & Ferguson (Hong Kong) Limited

(57) ABSTRACT

The present invention relates to an oridonin functionalized selenium nanoparticle, method of preparing and use thereof for anti-cancer and anti-inflammatory treatments. The present invention provides oridonin functionalized selenium nanoparticle that is stable, water soluble and storable.

8 Claims, 9 Drawing Sheets

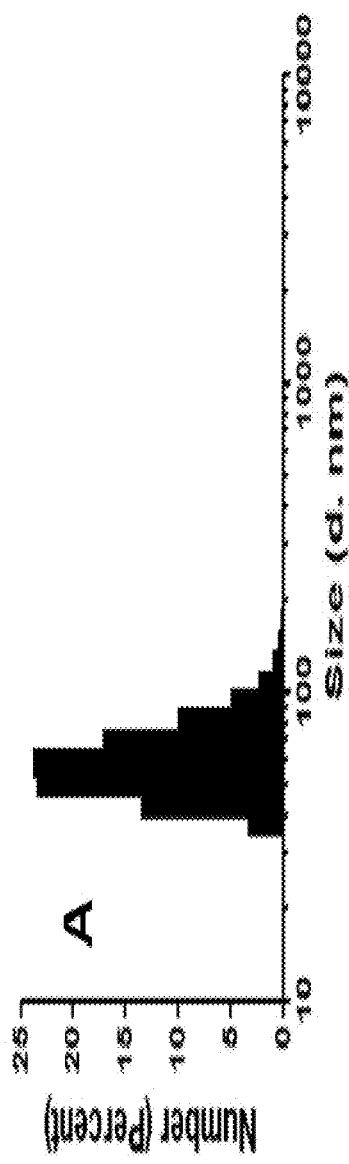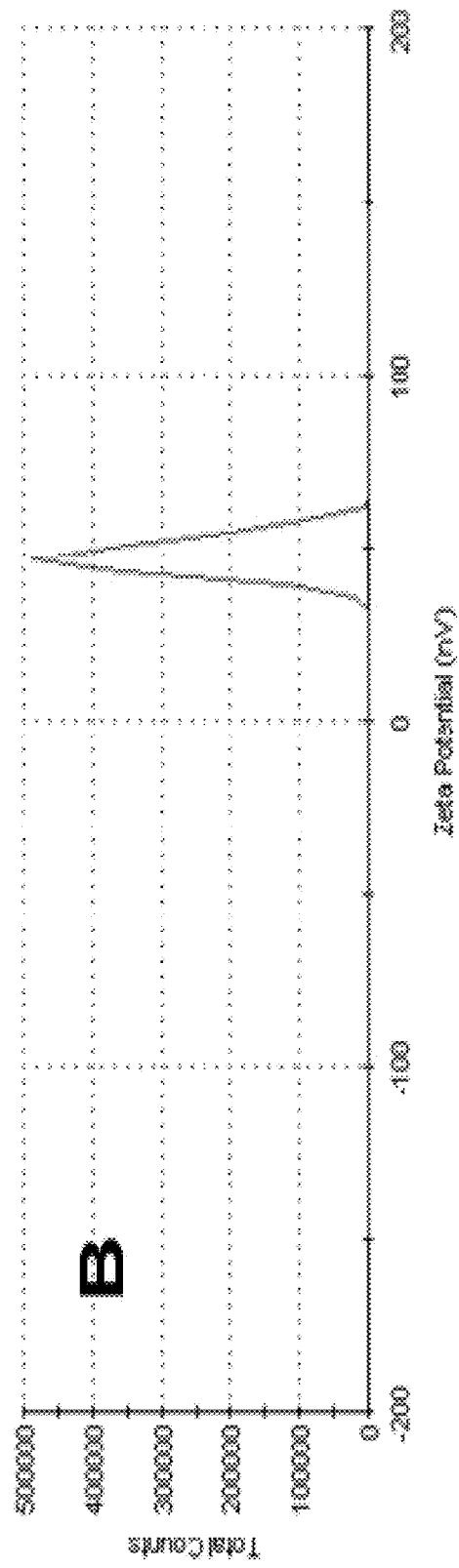
FIG. 4A
FIG. 4B

ORIDONIN FUNCTIONALIZED SELENIUM NANOPARTICLES AND METHOD OF PREPARATION THEREOF

CROSS REFERENCE TO RELATED APPLICATION

Pursuant to 35 U.S.C. §119, this is a non-provisional patent application which claims benefit from Chinese patent application number 201510101642.5 filed Mar. 5, 2015, and the disclosure of which is incorporated herein by reference.

FIELD OF THE INVENTION

The present invention relates to an oridonin functionalized selenium nanoparticle, method of preparing and use thereof for anti-cancer and anti-inflammatory treatments.

BACKGROUND

*Radbosia rubescens*, a herbal medicine, has been traditionally used in China for the treatment of pharyngitis and esophageal carcinoma. Oridonin, the main pharmacological active substance of *Rabdosia rubescens* with various pharmacological and physiological effects, has drawn a rising attention for cancer biologists due to its remarkable anti-tumor activities. It has been reported that oridonin can induce apoptosis or autophagy in various kinds of cancer cells, such as multiple myeloma cells, colorectal cancer cells, hepatoma carcinoma cell, prostate cancer cells, cervical carcinoma cells and oesophageal cancer cells. These reports demonstrate the potent anti-cancer activity of oridonin against different cancer cells.

However, the clinical application of oridonin remains limited due to its low water-solubility and low bioavailability. Therefore, there is a need to provide an alternative formulation of oridonin to overcome the problem of low water solubility of oridonin and to increase its efficacy and bioavailability.

Selenium (Se) is one of the essential trace mineral elements found in various tissues and organs in the human body. The mineral is particularly important for the enhancement of immune response and prevention of cancer development. Se is mostly linked to Se-dependent enzyme or selenoprotein function. The risk of many cancers is decreased with Se supplementation and the side effect of radiotherapy can also be reduced by Se supplementation, indicating the potential application of Se compounds in cancer prevention and cancer treatment. With reduced risk of Se toxicity and excellent bio-activities, selenium nanoparticles have been widely developed in recent years in life sciences, especially their potential use in cancer treatment. Firstly, selenium nanoparticles could be used as protection agents to protect the normal cells from the cytotoxicity of anti-cancer drugs. Secondly, selenium nanoparticles have strong cancer inhibition effects by inducing apoptosis of cancer cells. Thirdly, selenium nanoparticles could also be served as anti-angiogenesis agents, which could inhibit tumor growth by inhibiting new blood vessel formation.

Chitosan is a product resulting from the deacetylation of chitin, and is widely distributed in the carapace of shellfish or insects. Chitosan has been shown to associate with various pharmacological effects, including regulation of blood sugar level and blood fat level. As a natural product with high biocompatibility, safety, and biodegradability, chitosan is widely used in the field of medicine, food, chemical, cosmetic, water treatment, metal extraction and biomedical engineering.

SUMMARY OF THE INVENTION

Accordingly the presently claimed invention is to provide an oridonin functionalized selenium nanoparticle and method of preparing thereof. The oridonin functionalized selenium nanoparticle prepared by the present invention has an average particle size of 10-2000 nm. The present nanoparticle is water soluble, stable and possesses potential anti-cancer, anti-inflammatory anti-ageing and immunomodulatory activities. The present oridonin functionalized selenium nanoparticle, due to its high water solubility, can be safely administered to subject in need thereof for therapeutic applications.

According to an embodiment of the presently claimed invention, a method of preparing oridonin functionalized selenium nanoparticle comprises:

Preparing a solution of selenium-containing compound, a solution of oridonin, a solution of reducing agent and a solution of stabilizer;

Mixing the solutions of selenium-containing compound, oridonin, stabilizer and reducing agent to form the oridonin functionalized selenium nanoparticle, Wherein the oridonin functionalized selenium nanoparticle comprises 0.01-10 mM selenium, 0.01-10 mM oridonin, 0.001%-10% stabilizer and 0.1-100 mM reducing agent.

In one embodiment, the oridonin functionalized selenium nanoparticle comprises 0.5-5 mM selenium, 10-1,000 µM oridonin, 0.01%-1% stabilizer and 2-50 mM reducing agent. In a preferred embodiment, a molar ratio of oridonin and selenium of the oridonin functionalized selenium nanoparticle is 1:2. The oridonin functionalized selenium nanoparticle comprises 500 µM oridonin and 1 mM selenium.

In one embodiment, the solution of stabilizer is prepared by dissolving the stabilizer in 0.1%-10% acetic acid. The stabilizer comprises chitosan, hyaluronic acid, sodium hyaluronate, or a cellulose derivative or a combination thereof.

In one embodiment, the formation of the oridonin functionalized selenium nanoparticle is completed when increase in color intensity of the reaction mixture stops, wherein the reaction mixture turns into orange.

In one embodiment, the mixing of the solutions of selenium-containing compound, oridonin, stabilizer and reducing agent is performed by standing, agitation or sonication at 4° C.-100° C.

In one embodiment, the method further comprises dialyzing or centrifuging the mixed solutions after the reaction of forming of the oridonin functionalized selenium nanoparticle is completed to remove any excess unreacted solutions of selenium-containing compound, oridonin, stabilizer and reducing agent.

In one embodiment, concentration of selenium-containing compound solution to form the oridonin functionalized selenium nanoparticle is 1-1,000 mM. In another embodiment, the concentration of selenium-containing compound solution to form the oridonin functionalized selenium nanoparticle is 20-100 mM. In one embodiment, the solution of selenium-containing compound is an aqueous sodium selenite solution.

In one embodiment, concentration of oridonin to form the oridonin functionalized selenium nanoparticle is 1-100 mM. In another embodiment, the concentration of oridonin to form the oridonin functionalized selenium nanoparticle is 10-100 mM, 10-60 mM or 20-60 mM. In an embodiment, the oridonin solution to form the oridonin functionalized selenium nanoparticle is prepared by dissolving oridonin in an organic solvent, such as ethanol, methanol, ether or DMSO.

In one embodiment, concentration of the reducing agent to form the oridonin functionalized selenium nanoparticle is 1-1,000 mM or 20-100 mM. In another embodiment, the solution of reducing agent to form the oridonin functionalized selenium nanoparticle is ascorbic acid solution.

In one embodiment, concentration of the stabilizer solution to form the oridonin functionalized selenium nanoparticle is 0.1%-20% or 0.1%-5%.

In an embodiment, 1-1,000 mM solution of selenium-containing compound, 1-100 mM solution of oridonin, 1-1,000 mM solution of reducing agent and 0.1%-20% solution of stabilizer are prepared to form the oridonin functionalized selenium nanoparticle.

In another embodiment, 20-100 mM solution of selenium-containing compound, 10-60 mM solution of oridonin, 20-100 mM solution of reducing agent and 0.1%-5% solution of stabilizer are prepared to form the oridonin functionalized selenium nanoparticle.

BRIEF DESCRIPTION OF THE DRAWINGS

Embodiments of the present invention are described in more detail hereinafter with reference to the drawings, in which:

FIG. 4 shows size distribution (FIG. 4A) and zeta potential (FIG. 4B) of oridonin functionalized selenium nanoparticle of one embodiment of the present invention

DETAILED DESCRIPTION OF PREFERRED EMBODIMENTS

Figure 1:
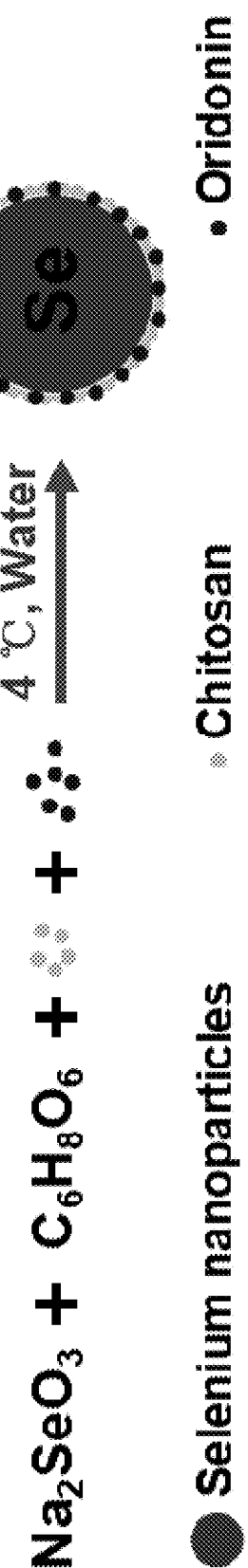
FIG. 1 shows the schematic diagram of one embodiment of the oridonin functionalized selenium nanoparticle of the present invention

Oridonin is a tetracycline diterpenoid isolated from Chinese herb *Rabdosia rubescens*, having a chemical structure of

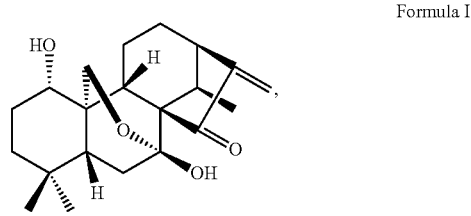

Formula I which is known to associate with anti-cancer and anti-inflammatory activities. The exomethylene conjugated cyclopentanon structure of oridonin is critical for its anti-cancer and anti-inflammatory activities. Oridonin is water insoluble. Water insolubility of oridonin limits its therapeutic application. The present invention provides a oridonin functionalized selenium nanoparticle and method of preparing thereof. The oridonin functionalized selenium nanoparticle of the present invention overcomes the water insolubility problem of oridonin, providing a means for safe administration of the compound to subject in need thereof and keeps the structure of oridonin intact.

The oridonin functionalized selenium nanoparticle of the present invention is a two layer structure, formed by redox reaction of selenium and oridonin in the presence of a stabilizer. Selenium forms spherical shaped nanoparticle, and the stabilizer and oridonin are assembled and absorbed on the surface of the selenium nanoparticles. In one embodiment, chitosan is used as a stabilizer in the present invention. Reduction of selenite then takes place in the presence of a reducing agent (e.g. ascorbic acid) and lead to the formation of selenium nanoparticles. The stabilizer is absorbed onto the surface of the selenium nanoparticle, and leaves the positive $NH^{3+}$ group on the surface. And simultaneously, oridonin is incorporated on the surface of the selenium nanoparticle of the present invention to form oridonin functionalized selenium nanoparticle. The present oridonin functionalized selenium nanoparticle solves the problem of water insolubility of oridonin and is shown to possess better biocompatibility, stability and pharmacological efficacy.

The present invention provides a method of preparing oridonin functionalized selenium nanoparticle comprises:
Providing a solution of selenium-containing compound, a solution of oridonin, a solution of reducing agent and a solution of stabilizer;
Mixing the solutions of selenium-containing compound, oridonin, and stabilizer to form a first mixture;
Adding the solution of reducing agent to the first mixture to form the nanoparticle,
Wherein the oridonin functionalized selenium nanoparticle comprises 0.01-10 mM selenium, 0.01-10 mM oridonin, 0.001%-10% stabilizer and 0.1-100 mM reducing agent.

In one embodiment, the oridonin functionalized selenium nanoparticle comprises 0.5-5 mM selenium, 0.01-1 mM oridonin, 0.01%-1% stabilizer and 2-50 mM reducing agent. In a preferred embodiment, a molar ratio of oridonin and selenium of the oridonin functionalized selenium nanoparticle is 1:2. The oridonin functionalized selenium nanoparticle comprises 500 μM oridonin and 1 mM selenium.

In one embodiment, the solution of stabilizer is prepared by dissolving the stabilizer in 0.1%-10% acetic acid. The stabilizer comprises chitosan, hyaluronic acid, sodium hyaluronate, or a cellulose derivative or a combination thereof. The solution of stabilizer may be filtered before mixing.

In one embodiment, the reaction of the formation of the oridonin functionalized selenium nanoparticle is completed when increase of color intensity of the mixed solution stops, wherein the reaction is completed when the mixed solution turns into orange.

In one embodiment, the mixing of the solutions of selenium, oridonin, stabilizer and reducing agent is performed by standing, agitation or sonication at 4° C.-100° C.

In one embodiment, the method further comprises dialyzing or centrifuging after the reaction of formation of the oridonin functionalized selenium nanoparticle is completed to remove any excess solutions of selenium-containing compound, oridonin, stabilizer and reducing agent. In one embodiment, the mixed solution is dialyzed with water for at least 48 hours to remove any unreacted solutions.

In one embodiment, concentration of selenium-containing compound solution to form the oridonin functionalized selenium nanoparticle is 1-1,000 mM. In another embodiment, the concentration of selenium-containing compound solution to form the oridonin functionalized selenium nanoparticle is 20-100 mM. In one embodiment, the selenium-containing compound comprises selenite, salt of selenite, selenite acid, selenium thiosulfate, selenium dioxide or a combination thereof. In one embodiment, the solution of selenium-containing compound is aqueous sodium selenite solution.

In one embodiment, concentration of oridonin to form the oridonin functionalized selenium nanoparticle is 1-100 mM. In another embodiment, the concentration of oridonin to form the oridonin functionalized selenium nanoparticle is 10-100 mM, 10-60 mM or 20-60 mM. In an embodiment, the oridonin solution to form the oridonin functionalized selenium nanoparticle is prepared by dissolving oridonin in an organic solvent, such as ethanol, methanol, DMSO or ether.

In one embodiment, concentration of the reducing agent to form the oridonin functionalized selenium nanoparticle is 1-1,000 mM or 20-100 mM. In another embodiment, the solution of reducing agent to form the oridonin functionalized selenium nanoparticle comprises ascorbic acid, gallic acid, asparagine, sodium sulphite or a combination thereof. In one embodiment, the reducing agent is ascorbic acid.

In one embodiment, concentration of the stabilizer solution to form the oridonin functionalized selenium nanoparticle is 0.1%-20% or 0.1%-5%.

In an embodiment, 1-1,000 mM solution of selenium-containing compound, 1-100 mM solution of oridonin, 1-1,000 mM solution of reducing agent and 0.1%-20% solution of stabilizer are prepared to form the oridonin functionalized selenium nanoparticle.

In another embodiment, 20-100 mM solution of selenium-containing compound, 10-60 mM solution of oridonin, 20-100 mM solution of reducing agent and 0.1%-5% solution of stabilizer are prepared to form the oridonin functionalized selenium nanoparticle. In one embodiment, the stabilizer is chitosan and the chitosan is dissolved in 1%-5% acetic acid to prepare 0.1%-5% chitosan solution for forming the oridonin functionalized selenium nanoparticle.

In one embodiment, the present method of preparing oridonin functionalized selenium nanoparticle comprises:

Dissolving a selenium-containing compound in water to obtain a 1-1,000 nM selenium-containing compound solution;

Dissolving oridonin in dimethyl sulfoxide to obtain a 1-100 mM oridonin solution;

Dissolving a reducing agent in water to obtain 1-1,000 mM reducing agent solution, wherein said reducing agent comprises at least one of ascorbic acid, gallic acid, asparagine or sodium sulphite;

Dissolving hyaluronic acid or sodium hyaluronate in water to obtain 0.1%-20% solution of hyaluronic acid or sodium hyaluronate;

Mixing solutions of selenium-containing compound, oridonin, hyaluronic acid or sodium hyaluronate to a first mixture;

Adding more water and the reducing agent solution to the first mixture and form a second mixture;

Allowing the second mixture to stand or to mix by agitating the second mixture or sonicating the second mixture until increase in the color intensity of the second mixture stops, wherein color change in the second mixture stops indicates that reaction to form oridonin functionalized selenium nanoparticle is completed. In one embodiment, the second mixture is mixed by standing for overnight, agitation for 1-3 h or sonication for 0.5-3 h at 4° C.-100° C. The second mixture turns into orange when water and reducing agent are added. In another embodiment, the concentration of the oridonin solution is 10-100 mM. In another embodiment, the concentration of the stabilizer is 0.1%-5%. In yet another embodiment, the method further comprises removing any unreacted solutions by dialyzing the oridonin functionalized selenium nanoparticle and/or centrifuging the oridonin functionalized selenium nanoparticle and washing pellet formed by said centrifuging. In one embodiment, the method further comprises drying, freeze-drying or drying under vacuum the oridonin functionalized selenium nanoparticle for storage. The present oridonin functionalized selenium nanoparticle may be stored under 4° C. The present oridonin functionalized selenium nanoparticle may be reconstituted in PBS solution before administration to a subject in need thereof.

The present invention also provides oridonin functionalized selenium nanoparticle formed by the above mentioned method. The present oridonin functionalized selenium nanoparticle comprising 0.01-10 mM selenium, 0.01-10 mM oridonin, 0.001%-10% stabilizer and 0.1-100 mM reducing agent, wherein the nanoparticle is a two layered structure in which the oridonin is incorporated onto the surface of the selenium nanoparticle stabilized by the stabilizer (FIG. 1). The oridonin functionalized selenium nanoparticle prepared according to the present invention has a particle size ranges from 10 nm-2000 nm. In one embodiment, the oridonin functionalized selenium nanoparticle of the present invention has an average particle size of 60 nm and an average zeta potential of 46 mV.

In the following description, the oridonin functionalized selenium nanoparticle, and methods of preparing said nanoparticle according to the present invention are set forth as below preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

The foregoing description of the present invention has been provided for the purposes of illustration and description. It is not intended to be exhaustive or to limit the invention to the precise forms disclosed. Many modifications and variations will be apparent to the practitioner skilled in the art.

EXAMPLE 1

Sodium selenite is dissolved in Milli-Q water to obtain 20-100 mM sodium selenite solution. Ascorbic acid is dissolved in Milli-Q water to obtain 20-100 mM ascorbic acid solution. Oridonin is dissolved in methanol to obtain 10-60 mM oridonin solution. Chitosan is dissolved in 1-5% acetic acid to obtain 0.1-5% chitosan solution. 50-200 μl sodium selenite solution is mixed with 10-50 μl oridonin and 10-500 μl chitosan solution to form the first mixture. Then, 300-1500 μl ascorbic acid solution is added to the first mixture and Milli-Q water is added to obtain a final volume of 1-10 ml for overnight reaction at 4° C. The final concentration of sodium selenite, oridonin, chitosan and ascorbic acid are 0.5-5 mM, 0.01-1 mM, 0.01%-1% and 2-50 mM, respectively. The excess reactants are removed by dialysis against Milli-Q water. After that, the obtained oridonin functionalized selenium nanoparticles can be stored at 4° C. in solution or stored as powders after centrifugation, freeze drying or vacuum drying.

EXAMPLE 2

Seleninic acid is dissolved in Milli-Q water to obtain 20-100 mM seleninic acid solution. Ascorbic acid is dissolved in Milli-Q water to obtain 20-100 mM ascorbic acid solution. Oridonin is dissolved in methanol to obtain 20-60 mM oridonin solution. Chitosan is dissolved in 1-5% acetic acid to obtain 0.1-5% chitosan solution. 50-200 μl seleninic acid solution is mixed with 10-60 μl oridonin and 100-500 μl chitosan solution to form the first mixture. Then, 300-1500 μl ascorbic acid solution is added to the first mixture and Milli-Q water is added to obtain a final volume of 1-10 ml for sonication treatment at room temperature. The final concentration of sodium selenite, oridonin, chitosan and ascorbic acid are 0.5-5 mM, 0.01-1 mM, 0.01%-1% and 2-50 mM, respectively. The excess reactants are removed by dialysis against Milli-Q water. After that, the obtained oridonin functionalized selenium nanoparticles can be stored at 4° C. in solution or stored as powders after centrifugation, freeze drying or vacuum drying.

EXAMPLE 3

Sodium selenite is dissolved in Milli-Q water to obtain 20-100 mM sodium selenite solution. Ascorbic acid is dissolved in Milli-Q water to obtain 20-100 mM ascorbic acid solution. Oridonin is dissolved in methanol to obtain 10-100 mM oridonin solution. Sodium hyaluronate is dissolved in Milli-Q water to obtain 0.1-5% sodium hyaluronate solution. 10-200 μl sodium selenite solution is mixed with 10-60 μl oridonin and 10-500 μl sodium hyaluronate solution to form the first mixture. Then, 300-1500 μl ascorbic acid solution is added to the first mixture and Milli-Q water is added to obtain a final volume of 1-10 ml for agitation treatment at room temperature. The final concentration of sodium selenite, oridonin, chitosan and ascorbic acid are 0.5-5 mM, 0.01-1 mM, 0.01%-1% and 2-50 mM, respectively. The excess reactants are removed by dialysis against Milli-Q water. After that, the obtained oridonin functionalized selenium nanoparticles can be stored at 4° C. in solution or stored as powders after centrifugation, freeze drying or vacuum drying.

EXAMPLE 4

Selenium dioxide is dissolved in Milli-Q water to obtain 1-1,000 mM selenium dioxide solution. Oridonin is dissolved in methanol to obtain 10-100 mM oridonin solution. Sodium sulfite is dissolved in Milli-Q water to obtain 1-1,000 mM sodium sulfite solution. Hyaluronic acid is dissolved in Milli-Q water to obtain 0.1-5% hyaluronic acid solution. 10-1000 μl selenium dioxide solution is mixed with 10-100 μl oridonin and 10-1000 μl hyaluronic acid solution to form the first mixture. Then, 0.1-10 ml sodium sulfite solution is added to the first mixture and Milli-Q water is added to obtain a final volume of 1-10 ml for agitation and heating treatment at 100° C. The excess reactants are removed by dialysis against Milli-Q water. After that, the obtained oridonin functionalized selenium nanoparticles can be stored at 4° C. in solution or stored as powders after centrifugation, freeze drying or vacuum drying.

EXAMPLE 5

Sodium selenite is dissolved in Milli-Q water to obtain 100 mM sodium selenite solution. Ascorbic acid is dissolved in Milli-Q water to obtain 100 mM ascorbic acid solution. Oridonin is dissolved in methanol to obtain 50 mM oridonin solution. Chitosan is dissolved in 1% acetic acid to obtain 0.1% chitosan solution. (A) 50 μl sodium selenite solution is mixed with 30 μl oridonin and 1000 μl chitosan solution to form the first mixture. Then, 200 μl ascorbic acid solution is added to the first mixture and Milli-Q water is added to obtain a final volume of 5 ml for overnight reaction at 4° C. (B) 75 μl sodium selenite solution is mixed with 90 μl oridonin and 750 μl chitosan solution to form the first mixture. Then, 300 μl ascorbic acid solution is added to the first mixture and Milli-Q water is added to obtain a final volume of 5 ml for overnight reaction at 4° C. (C) 50 ul sodium selenite solution is mixed with 150 μl oridonin and 500 μl chitosan solution to form the first mixture. Then, 200 ul ascorbic acid solution is added to the first mixture and Milli-Q water is added to obtain a final volume of 5 ml for overnight reaction at 4° C. The size distribution of the obtained oridonin functionalized selenium nanoparticles from conditions (A)-(C) is measured by Zetasizer Nano ZS particle analyzer (Malvern Instruments).

Figure 2A:
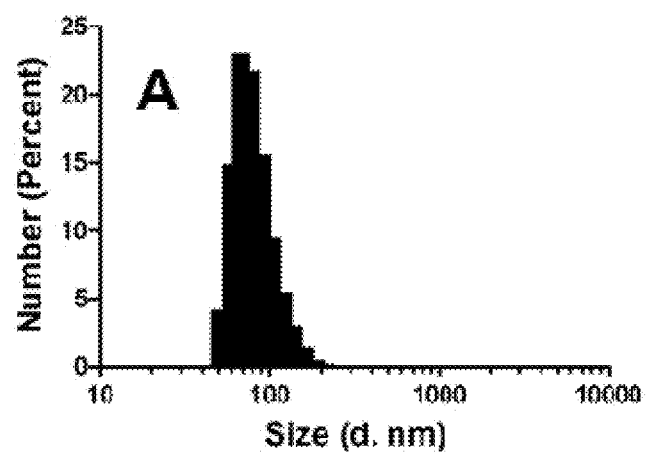
FIG. 2 shows particle size distribution of oridonin functionalized selenium nanoparticle of the present invention prepared by (A) 50 μl sodium selenite solution, 30 μl oridonin, 1,000 μl chitosan solution and 200 μl ascorbic acid solution; (B) 75 μl sodium selenite solution, 90 μl oridonin, 750 μl chitosan solution and 300 μl ascorbic acid solution; and (C) 50 μl sodium selenite solution, 150 μl oridonin, 500 μl chitosan solution and 200 μl ascorbic acid solution at 100 mM sodium selenite solution, 100 mM ascorbic acid solution, 50 mM oridonin solution and 0.1% chitosan solution
Figure 2B:
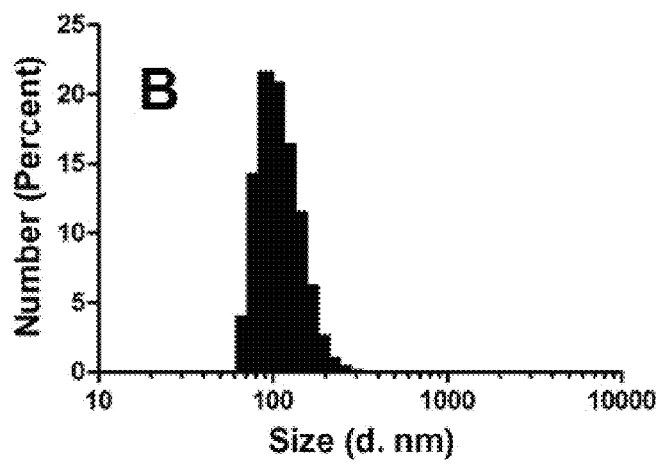
Figure 2C:
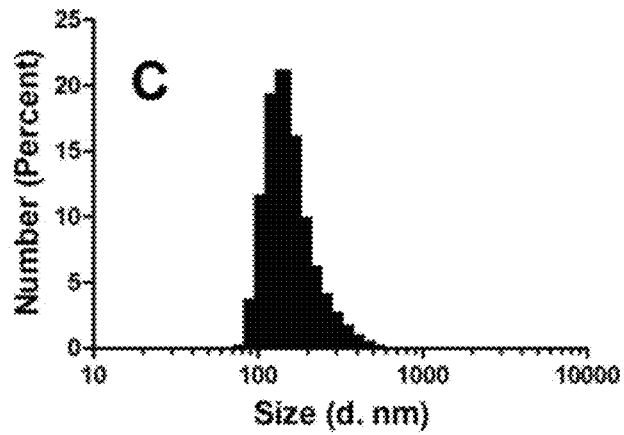

The size distribution of oridonin functionalized selenium nanoparticles obtained by condition (A) ranged from 45-250 nm, with an average diameter of 80 nm (FIG. 2A). The size distribution of oridonin functionalized selenium nanoparticles obtained by condition (B) ranged from 60-300 nm, with an average diameter of 100 nm (FIG. 2B). The size distribution of oridonin functionalized selenium nanoparticles obtained by condition (C) ranged from 80-600 nm, with an average diameter of 140 nm (FIG. 2C). Particle size of the nanoparticle is controlled by the concentration of reactants.

EXAMPLE 6

Sodium selenite is dissolved in Milli-Q water to obtain 50 mM sodium selenite solution. Ascorbic acid is dissolved in Milli-Q water to obtain 50 mM ascorbic acid solution. Oridonin is dissolved in methanol to obtain 50 mM oridonin solution. Chitosan is dissolved in 1% acetic acid to obtain 0.5% chitosan solution. 40 µl sodium selenite solution and 120 µl chitosan solution are mixed with 10 µl, 15 µl, 20 µl, 25 µl, 30 µl, 35 µl, 40 µl, 45 µl and 50 µl oridonin solution to form a set of nine first mixtures of different concentrations of oridonin. 320 µl ascorbic acid solution is added to each of the first mixtures and Milli-Q water is added to obtain a final volume of 2 ml for overnight reaction at 4° C. Under this reaction condition, 250 µM (10 µl oridonin), 375 µM (15 µl oridonin), 500 µM (20 µl oridonin), 625 µM (25 µl oridonin), 750 µM (30 µl oridonin), 875 µM (35 µl oridonin), 1,000 µM (40 µl oridonin), 1125 µM (45 µl oridonin) and 1250 µM (50 µl oridonin) oridonin are incorporated onto 1000 µM selenium nanoparticles. The average size and zeta potential of the obtained oridonin functionalized selenium nanoparticles are measured by Zetasizer Nano ZS particle analyzer (Malvern Instruments).

Figure 3A:
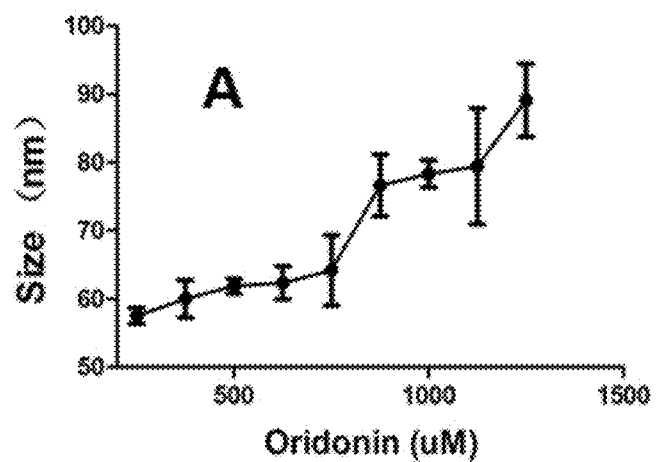
FIG. 3 shows zeta potential (FIG. 3A) and size distribution (FIG. 3B) of oridonin functionalized selenium nanoparticle of the present invention at 250 μM, 375 μM, 500 μM, 625 μM, 750 μM, 875 μM, 1,000 μM, 1125 μM and 1250 μM oridonin
Figure 3B:
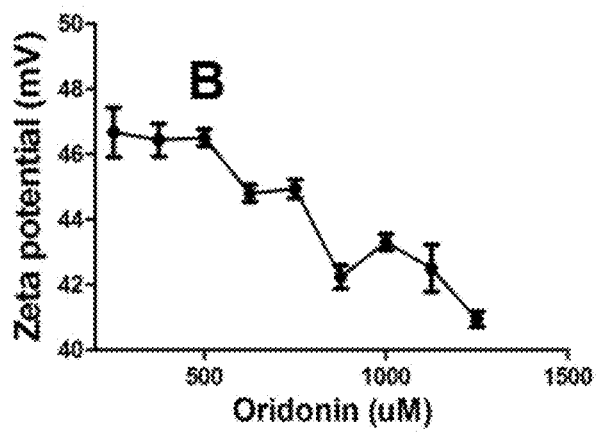

The average size of oridonin functionalized selenium nanoparticles increases with an increase in concentration of oridonin incorporated on selenium nanoparticles (FIG. 3A) and the average zeta potential of oridonin functionalized selenium nanoparticles decreases with the increased concentration of oridonin incorporated on selenium nanoparticles (FIG. 3B). The zeta potential of all tested nanoparticles is above 30 mV which is the standard value for a stable particle. The results show 500 µM oridonin incorporated onto 1000 µM selenium nanoparticles (in a molar ratio of 1:2) results in oridonin functionalized selenium nanoparticle with favorable particle size and stability of oridonin functionalized selenium nanoparticle.

EXAMPLE 7

Sodium selenite is dissolved in Milli-Q water to obtain 50 mM sodium selenite solution. Ascorbic acid is dissolved in Milli-Q water to obtain 50 mM ascorbic acid solution. Oridonin is dissolved in methanol to obtain 50 mM oridonin solution. Chitosan is dissolved in 1% acetic acid to obtain 0.5% chitosan solution. 100 µl sodium selenite solution and 300 µl chitosan solution are mixed with 50 µl oridonin solution to form the first mixture. 800 µl ascorbic acid solution is added in the first mixture and Milli-Q water is added to obtain a final volume of 5 ml for overnight reaction at 4° C. The excess reactants are removed by dialysis against Milli-Q water. The average size and zeta potential of the obtained oridonin functionalized selenium nanoparticles are measured by Zetasizer Nano ZS particle analyzer (Malvern Instruments).

The size of the obtained oridonin functionalized selenium nanoparticles ranged from 35 nm to 160 nm with an average diameter of 60 nm (FIG. 4A). In addition, the zeta potential of the obtained oridonin functionalized selenium nanoparticles ranges from 35 mV to 60 mV with an average zeta potential of 46 mV (FIG. 4B). It is recognized in the art that particles having zeta potential greater than 30 mV are considered to be stable. The results demonstrate the present nanoparticle is highly stable.

EXAMPLE 8

Sodium selenite is dissolved in Milli-Q water to obtain 50 mM sodium selenite solution. Ascorbic acid is dissolved in Milli-Q water to obtain 50 mM ascorbic acid solution. Oridonin is dissolved in methanol to obtain 50 mM oridonin solution. Chitosan is dissolved in 1% acetic acid to obtain 0.5% chitosan solution. 100 µl sodium selenite solution and 300 µl chitosan solution are mixed with 50 µl oridonin solution to form the first mixture. 800 µl ascorbic acid solution is added in the first mixture and Milli-Q water is added to obtain a final volume of 5 ml for overnight reaction at 4° C. The obtained oridonin functionalized selenium nanoparticles are centrifuged at 10,000×g for 15 mM and washed with water and dried to obtain oridonin functionalized selenium nanoparticles in powder form. The obtained powders of oridonin functionalized selenium nanoparticles are characterized by Fourier transform infrared spectroscopy (Equninox 55 IR Spectrometer)

Figure 5A:
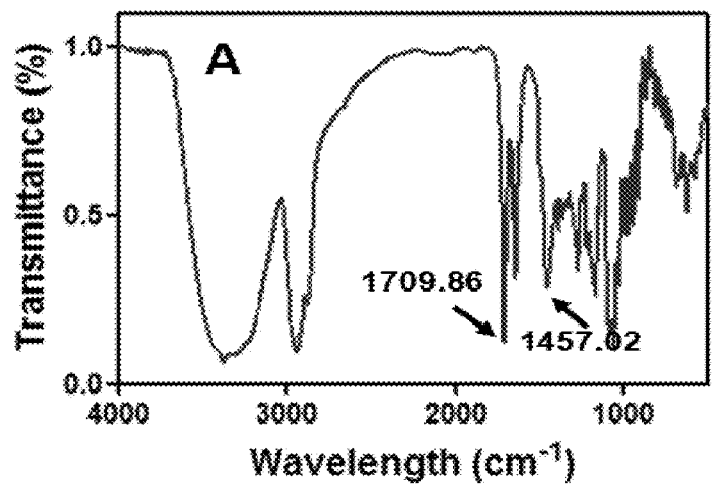
FIG. 5 shows the FTIR spectrum of oridonin (FIG. 5A), chitosan stabilized selenium nanoparticle (FIG. 5B, top spectrum) and oridonin functionalized selenium nanoparticle of one embodiment of the present invention (FIG. 5B, bottom spectrum)
Figure 5B:
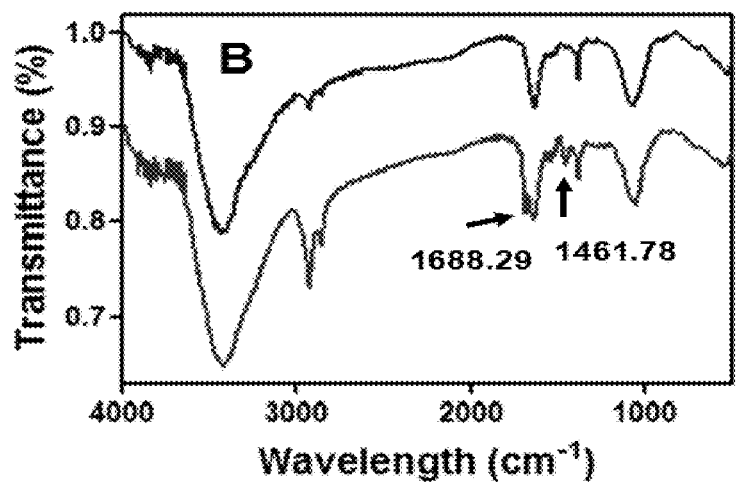

The spectrum of oridonin exhibits characteristic peaks 1709.86 cm$^{-1}$ and 1457.02 cm$^{-1}$ from the carbonyl group and hexatomic carbon ring of oridonin, respectively (FIG. 5A). Similarly, oridonin functionalized selenium nanoparticles shows the characteristic peaks for the carbonyl group and hexatomic carbon ring of oridonin in 1688.29 cm$^{-1}$ and 1461.78 cm$^{-1}$, respectively (FIG. 5B, bottom spectrum). These characteristic peaks could not be found in the spectrum of chitosan stabilized selenium nanoparticles without oridonin functionalization (FIG. 5B, top spectrum). This example demonstrates that the method of preparing a oridonin functionalized selenium nanoparticle of the present invention can incorporate oridonin onto the surface of selenium nanoparticle.

EXAMPLE 9

Sodium selenite is dissolved in Milli-Q water to obtain 50 mM sodium selenite solution. Ascorbic acid is dissolved in Milli-Q water to obtain 50 mM ascorbic acid solution. Oridonin is dissolved in methanol to obtain 50 mM oridonin solution. Chitosan is dissolved in 1% acetic acid to obtain 0.5% chitosan solution. 100 µl sodium selenite solution and 300 µl chitosan solution are mixed with 50 µl oridonin solution to form the first mixture. 800 µl ascorbic acid solution is added to the first mixture and Milli-Q water is added to obtain a final volume of 5 ml for overnight reaction at 4° C. The excess reactants are removed by dialysis against Milli-Q water. The morphology and size distribution of the obtained oridonin functionalized selenium nanoparticles are characterized by transmission electron microscope (TEM, Hitachi H-7650).

Figure 6A:
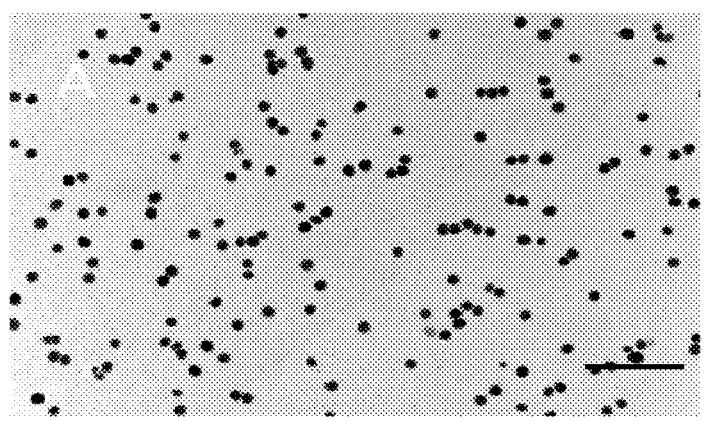
FIG. 6 shows TEM of oridonin functionalized selenium nanoparticle of one embodiment of the present invention at 500 nm (FIG. 6A) and 200 nm (FIG. 6B) scale
Figure 6B:
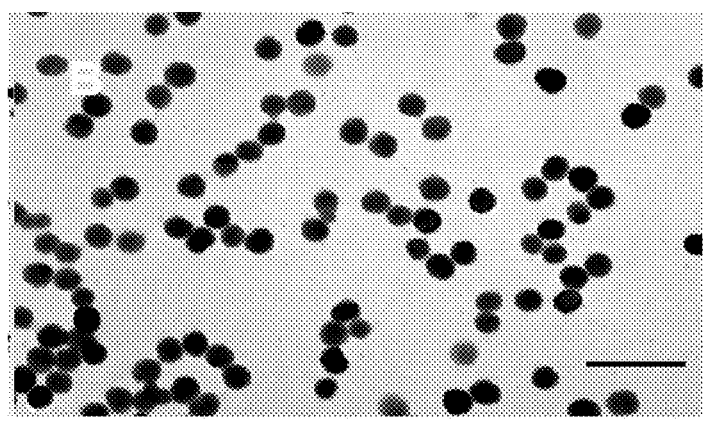

As seen in FIG. 6A at 500 nm scale and FIG. 6B at 200 nm scale, the oridonin functionalized selenium nanoparticles of the present invention are spherical with average diameter of 60 nm.

EXAMPLE 10

Sodium selenite is dissolved in Milli-Q water to obtain 50 mM sodium selenite solution. Ascorbic acid is dissolved in Milli-Q water to obtain 50 mM ascorbic acid solution. Oridonin is dissolved in methanol to obtain 50 mM oridonin solution. Chitosan is dissolved in 1% acetic acid to obtain 0.5% chitosan solution. 100 µl sodium selenite solution and 300 µl chitosan solution are mixed with 50 µl oridonin solution to form the first mixture. 800 µl ascorbic acid solution is added in the first mixture and Milli-Q water is added to obtain a final volume of 5 ml for overnight reaction at 4° C. The excess reactants are removed by dialysis against Milli-Q water.

The effects of oridonin functionalized selenium nanoparticles of the present invention on proliferation of cancer cells are determined. Viability of two oesophageal cancer cell lines KYSE-150 and EC-9706 cells upon exposure to oridonin functionalized selenium nanoparticles of the present invention is determined. MTT assays are used to examine the cell viability of the aforementioned cancer cell lines. The cells are seeded into 96 well plates with a density of $5 \times 10^3$ cells/well for 24 h and incubated with different concentration of the nanoparticles of the present invention for 48 h. MTT reagents (10 μL, 5 mg/mL) are added into each well for 4 h incubation, the medium is removed, and the cells are suspended in 150 μL DMSO for 10 min incubation. A spectrophotometer (TECAN, Switzer-land) is used to test absorbance at 490 nm. The percentage of cell viability is calculated using the following formula: Cell viability (%)=Absorbance (Oridonin functionalized selenium nanoparticles treated)/Absorbance (Control)×100.

Figure 7A:
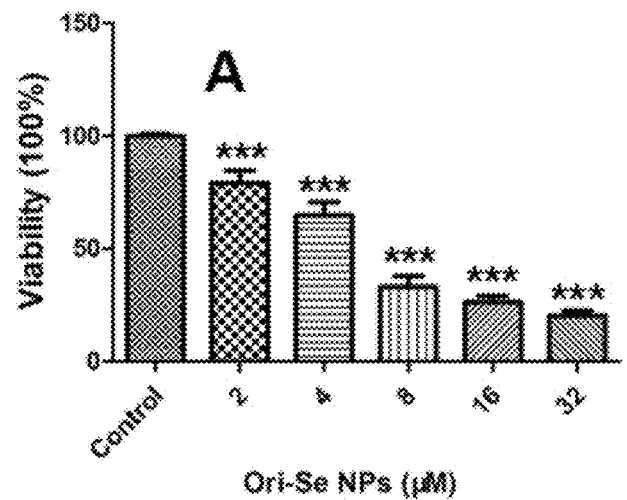
FIG. 7 shows effects of oridonin functionalized selenium nanoparticle of one embodiment of the present invention on viability of cancer cells KYSE-150 (FIG. 7A) and EC9706 (FIG. 7B)
Figure 7B:
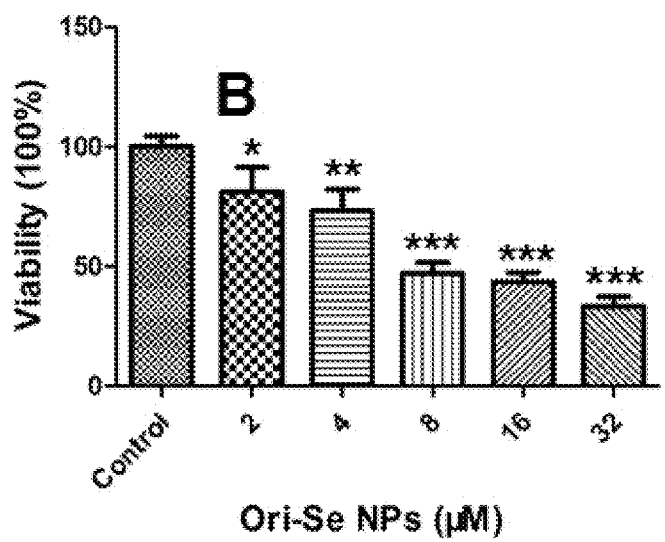

The viability of KYSE-150 cells decrease from 100±0.57% to 79.15±3.23%, 64.84±3.36%, 33.08±2.73%, 26.31±1.56% and 20.49±1.21% after 2 μM, 4 μM, 8 μM, 16 μM and 32 μM oridonin functionalized selenium nanoparticles treatment, respectively (FIG. 7A). The viability of EC-9706 cells decrease from 100±2.49% to 81.05±5.87%, 73.12±5.30%, 47.11±2.58%, 43.69±2.18% and 33.32±2.331% after 2 μM, 4 μM, 8 μM, 16 μM and 32 μM oridonin functionalized selenium nanoparticles treatment, respectively (FIG. 7B).

EXAMPLE 11

Sodium selenite is dissolved in Milli-Q water to obtain 50 mM sodium selenite solution. Ascorbic acid is dissolved in Milli-Q water to obtain 50 mM ascorbic acid solution. Oridonin is dissolved in methanol to obtain 50 mM oridonin solution. Chitosan is dissolved in 1% acetic acid to obtain 0.5% chitosan solution. 100 μl sodium selenite solution and 300 μl chitosan solution are mixed with 50 μl oridonin solution to form the first mixture. 800 μl ascorbic acid solution is added in the first mixture and Milli-Q water is added to obtain a final volume of 5 ml for overnight reaction at 4° C. The excess reactants are removed by dialysis against Milli-Q water.

The effect of the present nanoparticles on the viability and nitric oxide (NO) production of lipopolysaccharide (LPS) stimulated RAW264.7 macrophages are investigated to determine the anti-inflammatory activity of the present nanoparticles. MTT assays are used to test the cell viability of RAW264.7 macrophages expose to oridonin functionalized selenium nanoparticles. The cells are seeded into 96 well plates with a density of $5 \times 10^3$ cells/well for 24 h and incubated with different concentration of oridonin functionalized selenium nanoparticles for 1 h. LPS is added into the cell medium at a concentration of 100 ng/ml. After 24 h treatment, MTT reagents (10 μL, 5 mg/mL) are then added into each well for 4 h incubation, the medium is removed, and the cells are suspended in 150 uL DMSO for 10 mM incubation. A spectrophotometer (TECAN, Switzer-land) is used to test absorbance at 490 nm. The percentage of cell viability is calculated using the following formula: Cell viability (%)=Absorbance (Oridonin functionalized selenium nanoparticles treated)/Absorbance (Control)×100.

RAW264.7 cells are cultured at a density of $4 \times 10^5$ cells/mL in six well plates (2 mL/well). After incubation overnight, cells are pretreated with dexamethasone (DEX, 1 uM, positive control) or oridonin functionalized selenium nanoparticles for 1 h, and then 100 ng/mL LPS are added into the culture medium for 24 h stimulation. The cell culture supernatants are collected by 400×g centrifugation. Accumulated nitrite ($NO_2^-$) in cell culture supernatants is determined using a Nitrite/Nitrate colorimetric assay according to the manufacturer's instructions. The supernatants (50 μl) of each sample or standard substance (50 μl) are added into a 96-well plate, and then 50 μl Griess reagent I solution is added into each well for 10 min incubation followed by the addition of 50 μl Griess reagent II solution for 10 min incubation. The absorbance at 540 nm is immediately measured with a micro-plate reader (TECAN, Switzerland).

Figure 8A:
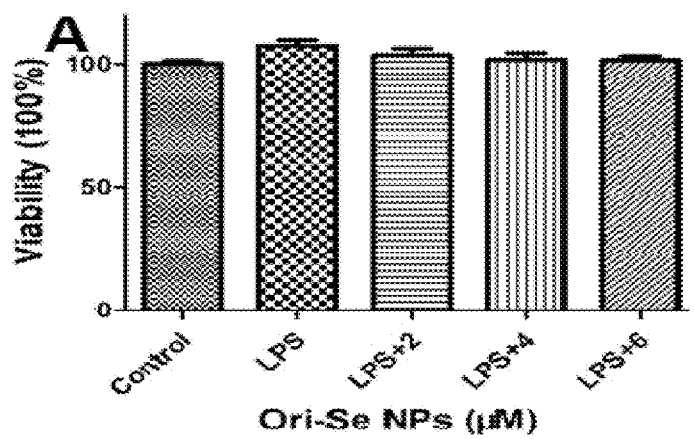
FIG. 8 shows effects of oridonin functionalized selenium nanoparticle of one embodiment of the present invention on the viability (FIG. 8A) and nitric oxide production (FIG. 8B) of LPS stimulated RAW264.7 macrophages
Figure 8B:
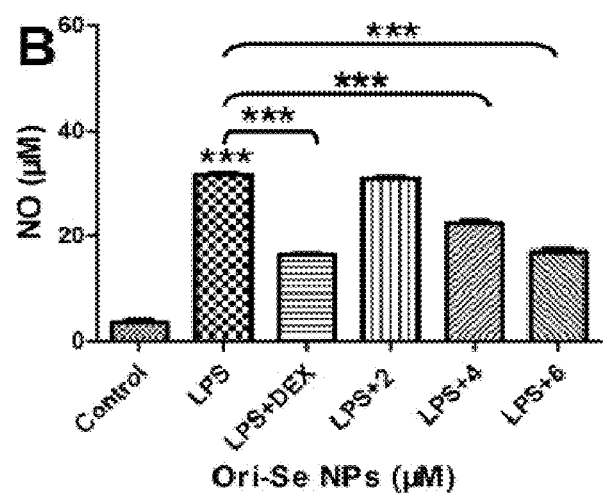

As shown in FIG. 8A, 2 μM, 4 μM and 6 μM oridonin functionalized selenium nanoparticles have no significant effects on the viability of LPS stimulated RAW264.7 macrophages. The nitrite level in the supernatant of RAW264.7 cells increase from 3.47±0.58 uM to 31.74±0.31 uM after 24 h LPS treatment, which is reversed to 16.63±0.20 uM with the pretreatment of 1 uM DEX (FIG. 8B). With the pretreatment of 2 μM, 4 μM and 6 μM oridonin functionalized selenium nanoparticles, the nitrite level in the supernatant of LPS stimulated RAW264.7 cells are 30.96±0.40 uM, 22.48±0.62 uM and 17.02±0.47 uM, respectively. Oridonin functionalized selenium nanoparticles of the present invention inhibits LPS induced NO production, demonstrating the anti-inflammation effects of the present oridonin functionalized selenium nanoparticles.

EXAMPLE 12

Figure 9:
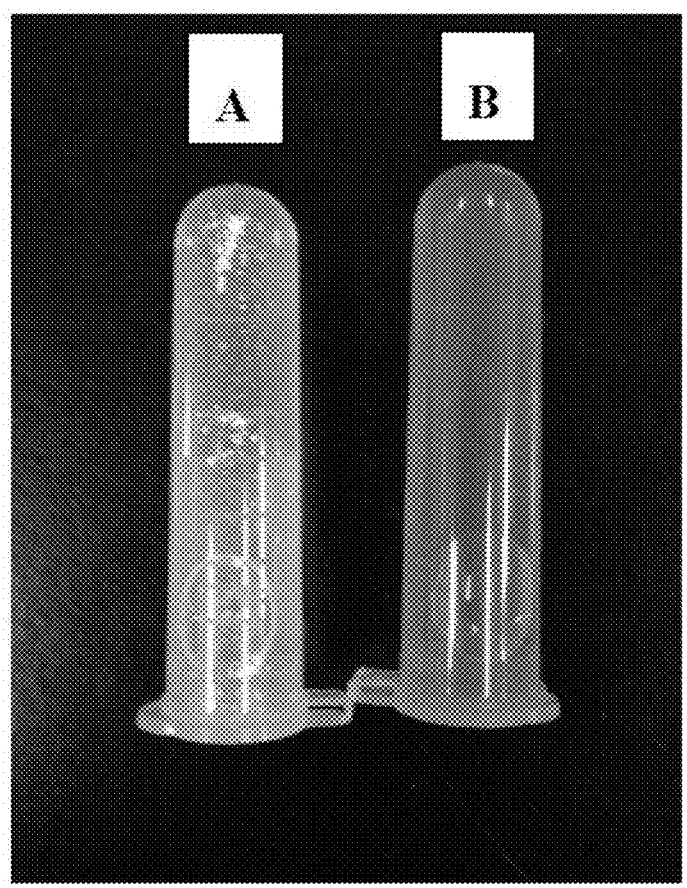
FIG. 9 shows pictures of oridonin (A) and oridonin functionalized selenium nanoparticle of the present application (B) dissolved in water

Water solubility of the present nanoparticle is examined. 1.44 mg of oridonin is dissolved in 4 ml water. As seen in FIG. 9, (A), oridonin is insoluble in water as expected. Large amount of white insoluble white oridonin powder is observed. On the other hand, oridonin functionalized selenium nanoparticle containing 1.68 mg of oridonin is prepared according to the present invention and dissolved in 4 ml water. The oridonin functionalized selenium nanoparticle is completely dissolved in water (FIG. 9, (B)). The oridonin functionalized selenium nanoparticle aqueous solution is orangey red in color and no insoluble residue is observed.

The above examples demonstrate the oridonin functionalized selenium nanoparticle of the present invention is stable, can be stored and highly water soluble. The nanoparticle also exhibit anti-cancer and anti-inflammatory properties.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

The invention claimed is:
1. A method of preparing oridonin functionalized selenium nanoparticle comprises:
   a) Providing a solution of selenium-containing compound, a solution of oridonin, a solution of reducing agent and a solution of stabilizer;
   b) Mixing the solutions of selenium-containing compound, oridonin, and stabilizer to form a first mixture;
   c) Adding the solution of reducing agent to the first mixture to form the nanoparticle,
   wherein the oridonin functionalized selenium nanoparticle comprises 0.01-10 mM selenium, 0.01-10 mM oridonin, 0.001%-10% stabilizer and 0.1-100 mM reducing agent.
2. The method of claim 1, wherein the selenium-containing compound comprises selenite, salt of selenite, selenite acid, selenium thiosulfate, selenium dioxide or a combination thereof.

3. The method of claim 1, wherein the reducing agent comprises ascorbic acid, gallic acid, asparagine, sodium sulphite or a combination thereof.

4. The method of claim 1, wherein the stabilizer comprises chitosan, hyaluronic acid, sodium hyaluronate, or a cellulose derivative or a combination thereof.

5. The method of claim 1 further comprises allowing the solutions of selenium-containing compound, oridonin, stabilizer and reducing agent to mix until color intensity in the solution mixture stops increasing, wherein the stopping of the increase in color intensity indicates completion of formation of nanoparticle.

6. An optimization oridonin functionalized selenium nanoparticle prepared by the method of claim 1.

7. The oridonin functionalized selenium nanoparticle of claim 6, wherein the nanoparticle has an average particle size of 35-160 nm and an average zeta potential of 35-60 mV.

8. The oridonin functionalized selenium nanoparticle of claim 6, wherein the selenium-containing compound is sodium selenite, the reducing agent is ascorbic acid and the stabilizer is chitosan.

\* \* \* \* \*